(12) United States Patent
Chiou et al.

(10) Patent No.: US 9,585,864 B2
(45) Date of Patent: Mar. 7, 2017

(54) ANTICANCER FORMULATION

(71) Applicant: National Dong Hwa University, Shoufeng (TW)

(72) Inventors: Tzyy-Wen Chiou, Hualien (TW); Horng-Jyh Harn, Taipei (TW); Shinn-Zong Lin, Taichung (TW)

(73) Assignee: National Dong Hwa University, Hualien (TW)

( * ) Notice: Subject to any disclaimer, the term of this patent is extended or adjusted under 35 U.S.C. 154(b) by 0 days.

(21) Appl. No.: 14/686,384

(22) Filed: Apr. 14, 2015

(65) Prior Publication Data

US 2015/0216836 A1 Aug. 6, 2015

Related U.S. Application Data

(63) Continuation of application No. 12/984,042, filed on Jan. 4, 2011, now abandoned.

(60) Provisional application No. 61/292,311, filed on Jan. 5, 2010.

(51) Int. Cl.
*A61K 31/343* (2006.01)
*A61K 47/34* (2006.01)
*A61K 9/00* (2006.01)

(52) U.S. Cl.
CPC .......... *A61K 31/343* (2013.01); *A61K 9/0024* (2013.01); *A61K 47/34* (2013.01)

(58) Field of Classification Search
None
See application file for complete search history.

(56) References Cited

U.S. PATENT DOCUMENTS

| 5,651,986 A | 7/1997 | Brem et al. | |
|---|---|---|---|
| 5,846,565 A * | 12/1998 | Brem | A61K 9/0085 424/422 |
| 2005/0255060 A1* | 11/2005 | Oblong | A61K 8/19 424/59 |
| 2006/0110469 A1* | 5/2006 | Luo | A61K 31/34 424/725 |

FOREIGN PATENT DOCUMENTS

| CA | 2615200 | 7/2009 |
|---|---|---|
| EP | 1 654 280 | 4/2006 |

OTHER PUBLICATIONS

Sin-cheng Lao and Simon Ming-yuen Lee. Danggui (当归 Angelica Sinensis), chapter 22 of Pharmacological Activity Based Quality Control of Chinese Herbs, 1st Edition, Editors: Shao-ping Li and Yi-Tao Wang. New York: Nova Science Publishers, Inc. 2008, pp. 417-440. ISBN: 978-1-60456-823-3.*
Chen et al., "The Induction of Orphan Nuclear Receptor Nur77 Expression by n-Butylenephthalide as Pharmaceuticals on Hepatocellular Carcinoma Cell Therapy," Mol. Pharmacol, 74:1046-1058 (2008).
Fleming, et al., "Pharmacokinetics of the Carmustine Implant", Clin. Pharmacokinet, 2002; 41(6): 403-419.
Information sheet for n-Butylidenephthalide from Alfa Aesar Chemical Company, downloaded from the Internet on Nov. 26, 2012, from the site: http://www.lancastersynthesis.com/en/GP100W.pgm?DSSTK=A10353&rnd=953520776.
Li et al., "Axl as a potential therapeutic target in cancer role of Axl in tumor growth, metastasis and angiogenesis," Oncogene, pp. 1-14 (2009).
Lin et al., "Orphan Nuclear Receptor, Nurr-77 Was a Possible Target Gene of Butylidenephthalide Chemotherapy on Glioblastoma Multiform Brain Tumor," Journal of Neurochemistry, 106: 1017-1026 (2008).
Tsai N-M, et al., "The Antitumor Effects of 1,10-15 Angelica Sinensis on Malignant Brain Tumors in Vitro and in Vivo," Clinical Cancer Research, vol. 11, No. 9, pp. 3475-3484 (May 2005).
Tsai, et al., "The natural compound n-butylidenephthalide derived from Angelica sinensis inhibits malignant brain tumor growth in vitro and in vivo", Journal of Neurochemistry, 2006, 99, 1251-1262.
Tsukamoto, et al., "Comparison of Larvicidal, Adulticidal and Acaricidal Activity of Two Geometrical Butylidenephthalide Isomers", Biol. Pharm. Bull. 29(3) 592-594 (2006).
Vajkoczy et al., "Dominant-Negative Inhibition of Axl Receptor Tyrosine Kinase Suppresses Brain Tumor Cell Growth and Invasion and Prolongs Survival," PNAS, 103(15): 5799-5804 (2006).
Walter K. A., et al. "Interstitial Taxol Delivered from a Biodegradavle Polymer Implant against Experimental Malgnant Glioma," Cancer Research, vol. 54, pp. 2207-2212 (Apr. 1994).

* cited by examiner

*Primary Examiner* — Frederick Krass
*Assistant Examiner* — Michael P Cohen
(74) *Attorney, Agent, or Firm* — Cesari and McKenna LLP

(57) ABSTRACT

This invention relates to a pharmaceutical formulation containing z-butylidenephthalide and a polymer, e.g., a polyanhydride. Also disclosed is use of this formulation to treat tumor.

9 Claims, No Drawings

ANTICANCER FORMULATION

CROSS REFERENCE TO RELATED APPLICATIONS

This is a continuation application of U.S. patent application Ser. No. 12/984,042, filed on Jan. 4, 2011, which claims priority to U.S. Provisional Application No. 61/292,311, filed Jan. 5, 2010. The contents of the prior applications are hereby incorporated by reference in their entirety.

BACKGROUND OF THE INVENTION n-Butylidenephthalide (Bdph) is a chemical compound isolated from *Angelica sinensis*. It can be used to treat various tumors, e.g., gliobastoma multiforme and breast cancer. See, e.g., Tsai et al., Clin. Cancer Res. 2005, 11(9): 3475-3484 and Tsai, et al., J Neurochem. 2006, 99(4): 1251-62. However, delivering n-butylidenephthalide to the cancer site in a selective and sustained manner is critical for its use in effective cancer therapy. This is especially important for treating brain cancer, where the drug is difficult to reach the disease area because of the blood brain barrier. There is a need of developing effective ways for delivering the drug.

SUMMARY

This invention is based on a discovery that a pharmaceutical formulation, from which n-butylidenephthalide, in particular, the Z-from (i.e. (Z)-n-butylidenephthalide, z-butylidenephthalide, and z-Bdph), can be gradually released over a long period, e.g., more than 30 days, and that z-Bdph, rather than E-from (i.e., (E)-n-butylidenephthalide, e-butylidenephthalide, and e-Bdph), has antitumor effects.

In one aspect, this invention features a pharmaceutical formulation, which contains (i) z-butylidenephthalide and (ii) a polymer, which are admixed together.

The polymer can be poly(lactic-co-glycolic acid), a chitosan, a collagen, a hydrogel, or a polyanhydride, e.g., a polyanhydride prepared from bis(p-carboxyphenozy)propane, bis(p-carboxyphenoxy)butane, bis(p-carboxyphenoxy)pentane, bis(p-carboxyphenoxy)heptane, bis(p-carboxyphenoxy)hexane, bis(p-carboxyphenoxy)octane, isophthalic acid, 1,4-phenylene dipropionic acid, dodecanedioic acid, oxalic acid, malonic acid, succinic acid, glutaric acid, adipic acid, pimelic acid, suberic acid, azelaic acid, sebacic acid, phthalic acid, isophthalic acid, terephthalic acid, or a mixture thereof.

An example of the formulation is a mixture of z-butylidenephthalide and polyanhydride p(CPP-SA), which is prepared from bis(p-carboxyphenoxy)propane (CPP) and the sebacic acid (SA). In the polyanhydride, the ratio between the bis(p-carboxyphenoxy)propane and the sebacic acid is preferably 1:2 to 1:10 (e.g., 1:4). The weight percentage of the z-butylidenephthalide is 3%-50% (e.g., 3%-20%, 10%, and 15%) of the formulation. The formulation can in form of powders, wafers, sheets, rods, microspheres, nanospheres, paste, or glue.

In another aspect, this invention features use of the above-described pharmaceutical formulation to treat tumor. Examples of tumor to be treated include, but are limited to, glioblastoma multiforme, lung cancer, hepatocellular carcinoma, colon cancer, melanoma, breast cancer, neuroblastoma, teratoma, and human leukemia.

Also within the scope of this invention is use of the above-described formulation in manufacturing medicament useful for treating tumor.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

One aspect of this invention relates to a pharmaceutical formulation containing n-butylidenephthalide, in particular, its z form, z-butylidenephthalide, and a polymer. The formulation can be used in inhibiting growth of tumors, such as glioblastoma multiforme.

z-butylidenephthalide used to practice this invention is commercially available, e.g., from Lancaster Synthesis Ltd. (UK). It can also be isolated from a chloroform extract of *Angelica sinensis*. See, e.g., Tsai et al., Clin. Cancer Res. 2005, 11(9): 3475-3484. The z-butylidenephthalide compound, either purchased or isolated, can be further purified by flash column chromatography, high performance liquid chromatography, crystallization, or any other suitable methods.

The polymer used to practice this invention either is commercially available or can be prepared by known methods in the art. For example, one can reflux a diacid compound in acetic anhydride to obtain a polyanhydride.

The polymer may be a copolymer. As an example, such a copolymer can be prepared from two different polyanhydride moieties using the melt polycondensation process. See, e.g., Domb et al., Journal of polymer science, 1987, 25: 3373-3386.

The obtained polymer can be purified by any suitable method and characterized by NMR, MS, or FT-IR.

To prepare the formulation of this invention, one can mix the z-butylidenephthalide and the polymer, e.g., a polyanhydride, at the desired ratio (e.g., 10 parts by weight the z-butylidenephthalide and 90 parts by weight the polyanhydride). As another example, one can dissolve the butylidenephthalide and polyanhydride in a solvent (e.g., methylene chloride) and then remove the solvent to provide a dry powder.

The thus obtained mixture can be further processed into various forms such as wafers, sheets, rods, microspheres, nanospheres, paste, or glue. For example, one can use a mold to compress the mixture into wafers.

The term "pharmaceutical formulation" is used herein to mean a composition which (i) is suitable for administration to a human being or other mammal or which can be treated, e.g. sterilized, to make it suitable for such administration, and (ii) comprises at least one drug (e.g., z-butylidenephthalide) and at least one of the above-mentioned polymers. The formulation can be part or all of any device that can deliver a drug, including pills, capsules, gels, depots, medical implantable devices (e.g., stents, including self-expanding stents, balloon-expandable stents, drug-eluting stents and stent-grafts, grafts (e.g., aortic grafts), artificial heart valves, cerebrospinal fluid shunts, pacemaker electrodes, endocardial leads, bioerodable implants and the like), and externally manipulated devices (e.g. drug devices and catheters, including catheters which can release a drug, e.g. as a result of heating the tip of the catheter). The pharmaceutical formulation may also include one or more other additives, for example pharmaceutically acceptable excipients, carriers, penetration enhancers, stabilizers, buffers or other materials physically associated with the drug and/or the polymer to enhance the deliverability of the dosage form and/or the effectiveness of the drug. The formulation may be, for example, a liquid, a suspension, a solid (such as a tablet, pill, and capsule, including a microcapsule), emulsion, micelle, ointment, gel, emulsion, depot (including a subcutaneously implanted depot), or coating on an implanted device, e.g. a stent or the like. The formulation can for example be applied externally, e.g. as a patch, or a device applied partly externally and partly implanted, or completely implanted or injected subcutaneously.

The term "drug" means a material which is biologically active in a human being or other mammal, locally and/or systemically. Examples of drugs are disclosed in the Merck Index, the Physicians Desk Reference, and in column 11, line 16, to column 12, line 58, of U.S. Pat. No. 6,297,337, and in paragraph 0045 of US 2003/0224974, the entire disclosures of which are incorporated by reference herein for all purposes. Drugs can for example be substances used for the treatment, prevention, diagnosis, cure or mitigation of a disease or illness, including vitamins and mineral supplements; substances which affect the structure or the function of a mammal; pro-drugs, which are substances which become biologically active or more active after they have been placed in a physiological environment; and metabolites of drugs. Examples of diagnostic agents are imaging agents containing radioisotopes, contrasting agents containing for example iodine, enzymes, fluorescent substances and the like.

The formulation of this invention may also contain suitable additives. These additives can be included in the formulation at any stage of the preparation of the formulation. The desired concentrations of the additives in the formulation for conferring the intended effect, as recognized by those skilled in the art, can be assayed using conventional methods.

The formulation of this invention, upon contact with fluid, releases z-butylidenephthalide—an antitumor agent. Thus, this invention also relates to a method of treating tumor by administering an effective amount of the formulation to a subject in need thereof. The butylidenephthalide in the formulation is slowly and continuously released into the adjacent tissue with in a certain period of time, e.g., 20, 30, 35, 40, 50, 60 days.

As used herein, the term "treating" or "treatment" is defined as the administration of an effective amount of the formulation to a subject, who has tumor, a symptom of tumor, a disease or disorder secondary to tumor, or a predisposition toward tumor, with the purpose to cure, alleviate, relieve, remedy, or ameliorate the tumor, the symptom of the tumor, the disease or disorder secondary to the tumor, or the predisposition toward the tumor.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model. A subject to be treated for a tumor, cancer, or other cellular proliferative disorder can be identified by standard diagnosing techniques for the disorder.

Tumor is a swelling or lesion formed by an abnormal growth of cells. It can be benign tumor or malignant tumor (i.e., cancer). Cancer refers to a class of diseases in which a group of cells display uncontrolled growth, invasion, and sometimes metastasis. Examples of cancer to be treated include, but are not limited to glioblastoma multiforme, lung cancer, hepatocellular carcinoma, colon cancer, melanoma, breast cancer, neuroblastoma, teratoma, and human leukemia.

The term "an effective amount" refers to an amount of a formulation or a compound which confers a therapeutic effect on the subject to be treated. The treatment method can be performed in vivo or ex vivo, alone or in conjunction with other drugs or therapy. In an in vivo approach, a compound or a formulation is administered to a subject. Generally, the compound or formulation is prepared in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

Preferably, the formulation can be subcutaneously, intramuscularly, intravenously, interstitially or intracranially implanted in a cancer patient. In one embodiment, the formulation, in various forms, can be implanted to the cancer site or in its proximity with or without the tumor tissue being removed.

The dosage required depends on the choice of the route of administration; the nature of the formulation; the nature of the patient's illness; the subject's size, weight, surface area, age, and sex; other drugs being administered; and the judgment of the attending physician. It can be adjusted by one skilled in the art, e.g., a nutritionist, dietician, or treating physician, in conjunction with the subject's response. Suitable dosages are in the range of 0.01-100 mg/kg. Variations in the needed dosage are to be expected in view of the variety of compounds available and the different efficiencies of various routes of administration.

The formulation can be used together with surgery or radiotherapy. It can also be used in combination with one or more other chemotherapeutic agents. The chemotherapeutic agents may be, for example, camptothecins such as topotecan, anthracycline antibiotics such as doxorubicin, alkylating agents such as cyclophosphamide, or antimicrotubule agents such as paclitaxel, temozolomide, or carmustin.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of Polymers

SA monomer was recrystallized twice from alcohol. 2.7 g SA monomer was refluxed in 60 ml acetic anhydride for 30 minutes (mins) at 135-140° C. under vacuum ($10^{-4}$ torr). The unreacted acetic anhydride was removed. The SA prepolymer was dried under vacuum at 60° C. and then dissolved in dry toluene. The solution was added to a 1:1 v/v mixture of dry ethyl ether and petroleum ether at a volume ratio of 1:10 and allowed to sit overnight to precipitate out the SA prepolymer (10:1 v/v). After the ethyl ether and petroleum ether were removed, the SA prepolymer was dried under vacuum.

3 g CPP monomers were refluxed with 50 ml acetic anhydride for 30 mins at 150° C. under vacuum ($10^{-4}$ torr).

After cooling, the reaction mixture was filtered. The filtrate was concentrated by removing some of unreacted acetic anhydride, and the CPP prepolymer was crystallized at 0° C. The remaining unreacted acetic anhydride was removed. The CPP prepolymer was washed with ether and dried under vacuum. DMF and dry ether (DMF: dry ether=1:9) were sequentially added to the CPP prepolymer. After about 12 hours, DMF and ether were removed and the CPP prepolymer crystal was dried under vacuum again.

CPP prepolymer and SA prepolymer at a ratio of 20:80 were charged into a glass tube (2×20 cm) and heated at 180° C. in an oil bath for 1 min. The pressure was reduced to $10^{-4}$ mmHg. The vacuum was eliminated at every 15 min throughout polymerization. The tube was washed with dichloromethane and then petroleum ether was added to precipitate out p(CPP-SA) copolymer, which was washed with anhydrous ether and dried under vacuum.

The p(CPP-SA) copolymer was characterized by IR and $^1$H NMR. In the IR spectroscopy, the characteristic signal of anhydride bond was observed at 1812.76 cm$^{-1}$. In the $^1$H NMR spectroscopy, the characteristic signals of aromatic protons of CPP were observed at 6.9-8.2 ppm, and the characteristic signal of methylene protons of SA was measured at 1.3 ppm. Further, the ratio of CPP and SA in the copolymer was identified as 1:4~1:5 according to characteristic peak intensity of CPP and SA in the $^1$H NMR spectroscopy.

p(CPP-SA) polymer was mixed with z-Bdph to provide a mixture containing 3% or 10% by weight z-Bdph. A mixture containing 97% p(CPP-SA) and 3% 1,3-bis(2-chloroethyl)-1-nitrosourea (BCNU) was also prepared. Each mixture was dissolved in methylene chloride at the concentration of 10% (w/v). The solution was dried under vacuum for 72 h. The thus-obtained dry powder was compressed to form z-Bdph p(CPP-SA) discs (100 mg/disc) using a stainless steel mold (internal diameter, 13 mm) under light pressure from a Carver Press at 200 psi as described in Walter et al., Cancer Res. 1994, 54(8): 2207-12; Leong et al., J Biomed Mater Res. 1985, 19(8): 941-55; and Storm et al. J Neurooncol. 2002, 56(3): 209-17. BCNU p(CPP-SA) discs of the same size were also prepared by compression molding.

Example 2

Release Kinetics z-Bdph-p(CPP-SA) discs were placed in scintillation vials having 1.0 ml of 0.1 M phosphate-buffered saline (pH 7.4) and 1.0 ml n-octanol and incubated at 37° C. The solution was replaced by fresh buffer at various time points. Absorption at the wavelength of 310 nm was measured using a spectrophotometer to determine the concentration of z-Bdph in the buffer as described in Weingart et al., Int. J. Cancer. 1995, 62(5): 605-9. Sustained release of z-Bdph was observed.

Example 3

In Vitro Controlled Release and Cytotoxic Effects

Assays were conducted to examine the growth inhibitory effects of p(CPP-SA)-10% z-Bdph on RG2 rat glioblastoma multiforme (GBM) cells. RG2 cells were treated with 10% Bdph-wafer for 24 hrs. Cell viability were determined by MTT assay. It was found that the growth inhibitory effects of p(CPP-SA)-10% z-Bdph were 50% compared with control. In addition, the morphology of GBM cells gradually changed and detaching of the cells from the bottom of culture plate was observed after treatment. Compared to untreated cells, most of the detached GBM cells were apoptotic after p(CPP-SA)-10% z-Bdph treatment.

Note that data were expressed as the mean±SD or SE (standard deviation and standard error, respectively) from three independent experiments. Statistical significance was analyzed by Student's t-test and Mantel-Cox test. The survival analysis was performed using the Kaplan-Meier method. A P value of <0.05 was considered significant.

Example 4

Apoptotic Pathways and Nurr Translocation Induced by p(CPP-SA)-z-Bdph

To confirm the results of the oligodeoxynucleotide-based microarray analysis, expression of the orphan receptors NOR-1, Nurr1, and Nur77 was examined in z-Bdph-treated RG2 cells by RT-PCR.

RG2 cells were incubated with IC$_{50}$ concentration of z-Bdph for various time periods (0, 0.5, 1, 3, and 6 h). After incubation, cells were collected and total RNA isolated. Expression of GADPH was used as an internal control.

After treatment with z-Bdph, the mRNA expression of Nurr77 was induced in the cells in a time-dependent manner. Nurr77 mRNA expression was significantly induced from half hour after z-Bdph treatment to 6 hours after the treatment. Nur77, which was highly induced after z-Bdph treatment, has been implicated in growth inhibition and apoptosis, suggesting that Nur77 induction could be an early event of z-Bdph-induced apoptosis in GBM cells.

Whether translocation of Nur77 occurred in response to z-Bdph was examined. DBTRG-05NG cells (human GBM cells) were treated with Bdph (100 µg/mL) for 24 hours, then immunostained with anti-Nur77 antibody followed by corresponding Rhodamine-conjugated anti-IgG secondary antibody. Simultaneously, cells were stained with DAPI to display the nuclei. The fluorescent images were visualized with a fluorescence microscope. The result showed that, Nur77 was much more abundant in the nucleus than in the cytosol. After treatment of z-Bdph for 24 hours, Nur77 was translocated from the nucleus to the cytoplasm.

For further confirmation, cytosolic and nucleus fractions of cells were examined by Western blot analysis. RG2 cells were plated on 10 cm dishes and incubated to 90% confluence. The cells were treated with Bdph (100 µg/ml) for different time periods (0, 6, 12, 24 and 48 hours). The cells were harvested, and nuclear and cytoplasmic fractions were isolated. Western blot analysis showed that Nur77 was predominantly localized in the nucleus in the absence of z-Bdph treatment.

Finally, signaling pathways involved in z-Bdph-induced Nur77 gene expression were investigated. RG2 cells were treated with Bdph (100 µg/ml) for various time periods (0, 15, 30, 60, and 180 mins). Western blot analysis showed that JNK, AKT, ERK were significantly phosphorylated after z-Bdph treatment for 1 hour. Moreover, MTT assay results showed that cell viability increased after the cells were pretreated with a pJNK inhibitor at 5-20 nM and treated with z-Bdph.

Example 5

Animal Studies

Male F344 rats (230-260 g) and male Foxn1 nu/nu mice (10-12 weeks) were obtained from National Laboratory Animal Center (Taipei, Taiwan). All procedures were performed in compliance with the standard operation procedures of the Laboratory Animal Center of National Tau Hwa University (Hualien, Taiwan) and China Medical University Hospital (Taichung, Taiwan). RG2 cells and DBTRG-05MG cells were used in animal experiments to monitor the antitumor activities of p(CPP-SA)-3% or 10% z-Bdph formulations and p(CPP-SA)-3% BCNU.

Syngeneic F344 rats received subcutaneous back implants of RG2 cells. Animals were treated by subcutaneous implant with p(CPP-SA)-3%, p(CPP-SA)-10% z-Bdph formulations, p(CPP-SA)-3% BCNU, or polymer alone at least 1.5 cm removed from the original injection site after the tumor cell implantation.

In addition, Foxn1 nu/nu mice received subcutaneous implantation of DBTRG-05MG cells, and subcutaneous implantation of p(CPP-SA)-3%, p(CPP-SA)-10% z-Bdph formulations, p(CPP-SA)-3% BCNU, or polymer alone at least 1.5 cm removed from the original injection site after the tumor cell implantation.

Tumor sizes were measured by using a caliper and the volume was calculated as L×H×W×0.5236. Animals were sacrificed when the volumes of tumor exceeded 25 $cm^3$ in rat and 1000 $mm^3$ in mice. That date was used to calculate the final survival date for the rats and mice.

Example 6

Therapeutic Effects of p(CPP-SA)-z-Bdph in Animal Model

RG2 cells ($5 \times 10^6$) were implanted subcutaneously into the hind flank region of F344 rats. After five days of RG2 cell transplantation, the rats were treated subcutaneously with p(CPP-SA)-3% z-Bdph, p(CPP-SA)-10% z-Bdph, p(CPP-SA) alone, or p(CPP-SA)-3% BCNU. Significant tumor growth inhibition was observed for the p(CPP-SA)-10% z-Bdph treated group, as compared with the p(CPP-SA)-3% z-Bdph treated group, p(CPP-SA)-3% BCNU treated group, and p(CPP-SA) treated group ($p<0.005$).

Average tumor sizes at day 30 were 2070.79±784.90 $mm^3$ for the control (untreated) group, 1586.30±243.69 $mm^3$ in the p(CPP-SA) treated group, 346.71±521.68 $mm^3$ in the p(CPP-SA)-3% z-Bdph treated group, 87.89±167.44 $mm^3$ in the p(CPP-SA)-10% z-Bdph treated group, and 357.48±27.30 $mm^3$ in the p(CPP-SA)-3% BCNU treated group.

The immunohistochemical stain of ki-67, indicating cell proliferation, showed a significant decrease of cell proliferation in the p(CPP-SA)-10% z-Bdph treated group. In addition, the immunohistochemical stain of caspase, indicating cell apoptosis, showed a significant increase of cell apoptosis in the p(CPP-SA)-10% z-Bdph treated group.

Finally, no drug related toxicities, as evaluated by the body weights and the histological analyses of various organs, were observed in the animals in the p(CPP-SA)-10% z-Bdph treated group. In contrast, significant body weight loss was observed in the p(CPP-SA)-3% BCNU treated group.

Example 7

Therapeutic Effects of p(CPP-SA)-z-Bdph in Xenograft Tumor Growth

Foxn1 nude mice were inoculated with human DBTRG-05MG cells ($2 \times 10^6$) and implanted with p(CPP-SA)-z-Bdph (0%, 3% 10%) at day 5. Significant suppressions of tumor growth in the 3% and 10% z-Bdph-wafer treated groups was observed. The mean values of tumor sizes at day 39 were 1098.46±170.11 in the control group, 605.8±98.8 $mm^3$ in p(CPP-SA)-3% z-Bdph treated group, and 504.4±38.9 $mm^3$ in p(CPP-SA)-10% z-Bdph treated group ($p<0.05$).

Example 8 z-Bdph Inhibits Migration and Invasion of Human Glioblastoma Multiformis

The invasion of DBTRG-05MG cells was examined using a BioCoat matrigel invasion chamber system (BD Bioscience, Bedford, Mass.). The BD matrigel Matrix is composed of laminin, collagen IV, nidogen/entrctin, and proteoglycan on polyethylene terephthalate (PET) membranes containing 8 µm pores. In the in vitro migration assay, low pore density PET track-etched membrane on Falcon culture insert (BD Bioscience) was applied. The membrane was placed between the upper and lower wells of a Matrigel chamber or Falcon culture inserts. The cells were first resuspended in PRMI 1640 containing 10% fetal bovine serum and seeded into the upper wells of the chamber (50,000 cells per well). After incubating for 24 hours at 37° C., the cells that invaded or migrated through the membrane were stained with Liu stain (Handsel Technologies, Inc., Taipei, Taiwan) and counted under a microscopy. Each experiment was repeated thrice.

The above-described system was used to examine the effects of z-Bdph on the migration and invasion of DBTRG-05MG cells (human GBM). It was found that z-Bdph inhibited migration and invasion of DBTRG-05MG cells in a dose dependent manner.

Example 9 z-Bdph Inhibits Tumor Migration and Invasion Via Repressing Axl

Reverse transcriptase-polymerase chain reaction (RT-PCR) was used to examine the effect of z-Bdph on the gene expression profile in GBM cells to elucidate the possible mechanisms of z-Bdph's inhibition of malignant brain tumor. It was found that the mRNA expressions of Axl receptor tyrosine kinase (RTK) were down-regulated in the presence of z-Bdph.

Further, the over-expression of Axl (i.e., by transfecting a pcDNA3.0-Axl plasmid into the GBM cells) could reverse the inhibitory effect of z-Bdph on Axl mediated proliferation, migration and invasion of the GBM cells.

Western Blot assays were also carried out to examine the Axl protein level of the GBM cells in the presence of z-Bdph. The results show that the Axl protein level was reduced.

It is now well established that protein tyrosine kinases play an important role in the regulation of cellular proliferation and differentiation and in the genesis of many neoplasias including human glioma. Axl was reported to be involved in tumor migration and invasion. The above results suggested that z-Bdph inhibited the protein expression of Axl receptor tyrosine kinase and thereby inhibited migration and invasion of the GBM cells.

Other Embodiments

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. An implantable pharmaceutical formulation comprising z-butylidenephthalide, and a polymer admixed with the z-butylidenephthalide, wherein the pharmaceutical formulation does not include e-butylidenephthalide, and wherein the polymer is a polyanhydride prepared from bis(p-carboxyphenoxy)propane (CPP) and sebacic acid (SA), the ratio of CPP to SA being 20:80.

2. The pharmaceutical formulation of claim 1, wherein the weight percentage of the z-butylidenephthalide is 3%-50% of the formulation.

3. The pharmaceutical formulation of claim 2, wherein the weight percentage of the z-butylidenephthalide is about 10% of the formulation.

4. The pharmaceutical formulation of claim 2, wherein the formulation is a wafer.

5. A method of treating a tumor comprising administering to a subject in need thereof an effective amount of the pharmaceutical formulation of claim 1.

6. The method of claim 5, wherein the tumor is glioblastoma multiforme.

7. The method of claim 5, wherein the weight percentage of the z-butylidenephthalide is 3%-50% of the formulation.

8. The method of claim 7, wherein the weight percentage of the z-butylidenephthalide is about 10% of the formulation.

9. The method of claim 5, wherein the pharmaceutical formulation is intracranially implanted in the subject.

* * * * *